United States Patent
Kenney et al.

(10) Patent No.: US 7,897,379 B2
(45) Date of Patent: Mar. 1, 2011

(54) DEVICE AND METHOD FOR REDUCING BUBBLE FORMATION IN CELL CULTURE

(75) Inventors: David A. Kenney, Lunenburg, MA (US); Gregory R. Martin, Acton, ME (US); Allison J. Tanner, Portsmouth, NH (US); Joseph C. Wall, Southborough, MA (US)

(73) Assignee: Corning Incorporated, Corning, NY (US)

( * ) Notice: Subject to any disclaimer, the term of this patent is extended or adjusted under 35 U.S.C. 154(b) by 1039 days.

(21) Appl. No.: 11/710,815

(22) Filed: Feb. 26, 2007

(65) Prior Publication Data

US 2008/0206857 A1    Aug. 28, 2008

(51) Int. Cl.
C12M 1/21     (2006.01)
C12M 3/00     (2006.01)
C12M 1/24     (2006.01)
C12N 5/071    (2010.01)

(52) U.S. Cl. ............... 435/301.1; 435/297.5; 435/304.2; 435/372

(58) Field of Classification Search ........... 435/301.1, 435/284, 296, 297.5, 304.2, 372
See application file for complete search history.

(56) References Cited

U.S. PATENT DOCUMENTS

| | | | |
|---|---|---|---|
| 4,225,671 A | 9/1980 | Puchinger et al. | 435/71 |
| 4,296,205 A | 10/1981 | Verma | 435/240 |
| 4,661,455 A | 4/1987 | Hubbard | 435/240 |
| 4,734,373 A | 3/1988 | Bartal | 435/296 |
| 4,748,124 A | 5/1988 | Vogler | 435/240.241 |
| 4,770,854 A * | 9/1988 | Lyman | 422/102 |
| 4,839,292 A | 6/1989 | Cremonese | 435/313 |
| 4,935,371 A * | 6/1990 | Rickloff | 435/304.3 |
| 4,938,196 A | 7/1990 | Hoshi et al. | 123/489 |
| 4,945,203 A | 7/1990 | Soodak et al. | 219/121.64 |
| 5,026,650 A | 6/1991 | Schwarz et al. | 435/286 |
| 5,047,347 A | 9/1991 | Cline | 435/296 |
| 5,079,168 A | 1/1992 | Amiot | 437/284 |
| 5,139,946 A | 8/1992 | Howell et al. | 435/240.2 |
| 5,149,649 A | 9/1992 | Miyamori et al. | 435/240.242 |
| 5,153,131 A | 10/1992 | Wolf et al. | 435/240.24 |
| 5,310,676 A | 5/1994 | Johansson et al. | 435/285 |
| 5,330,908 A | 7/1994 | Spaulding | 435/240.24 |
| 5,416,022 A | 5/1995 | Amiot | 435/284 |

(Continued)

FOREIGN PATENT DOCUMENTS

EP    155237 B1    5/1989

(Continued)

OTHER PUBLICATIONS

E. Metzen, M. Wolff, J. Fandrey, and W. Jelkmann, Pericellular PO2 and O2 consumption in monolayer cell cultures, Respiration Physiology 100 (1995) 101-106.

(Continued)

Primary Examiner — Walter D Griffin
Assistant Examiner — Lydia Edwards
(74) Attorney, Agent, or Firm — Susan S. Wilks

(57) ABSTRACT

A device for minimizing the formation of bubbles or foam in cell culture is disclosed. The device has a manifold which directs the inflow of cells and cell culture media into a cell culture vessel so as to allow for displaced air or gas to vent from the cell culture vessel without mixing with the incoming cell culture media, thereby preventing the mixing of air and cell culture media and minimizing the formation of bubbles or foam inside the cell culture vessel.

21 Claims, 5 Drawing Sheets

U.S. PATENT DOCUMENTS

| | | | |
|---|---|---|---|
| 5,437,998 A | 8/1995 | Schwarz et al. | 435/286 |
| 5,476,573 A | 12/1995 | Hirose et al. | 202/197 |
| 5,523,236 A | 6/1996 | Nuzzo | 435/304.1 |
| 5,527,705 A | 6/1996 | Mussi et al. | 435/297.1 |
| 5,565,353 A * | 10/1996 | Klebe et al. | 435/383 |
| 5,589,112 A | 12/1996 | Spaulding | 264/413 |
| 5,597,731 A | 1/1997 | Young et al. | 435/284.1 |
| 5,602,028 A | 2/1997 | Minchinton | 435/401 |
| 5,627,070 A | 5/1997 | Gruenberg | 435/786.5 |
| 5,650,325 A * | 7/1997 | Spielmann | 435/299.1 |
| 5,658,797 A | 8/1997 | Bader | 435/284.1 |
| 5,686,301 A | 11/1997 | Falkenberg et al. | 435/297.1 |
| 5,686,304 A | 11/1997 | Codner | 435/325 |
| 5,693,537 A | 12/1997 | Wilson et al. | 435/401 |
| 5,702,941 A | 12/1997 | Schwarz | 435/243 |
| 5,714,384 A | 2/1998 | Wilson et al. | 435/401 |
| 5,763,261 A | 6/1998 | Gruenberg | 435/286.5 |
| 5,763,275 A | 6/1998 | Nagels et al. | 435/373 |
| 5,763,279 A | 6/1998 | Schwarz et al. | 435/383 |
| 5,783,440 A | 7/1998 | Stevens | 435/304.3 |
| 5,786,215 A | 7/1998 | Brown et al. | 435/401 |
| 5,801,054 A | 9/1998 | Kiel | 435/297.5 |
| 5,912,177 A | 6/1999 | Turner et al. | 435/455 |
| 5,924,583 A | 7/1999 | Stevens et al. | 215/40 |
| 6,107,085 A | 8/2000 | Coughlin et al. | 435/299.1 |
| 6,114,165 A | 9/2000 | Cai et al. | 435/304.3 |
| 6,190,913 B1 | 2/2001 | Singh | 435/394 |
| 6,297,046 B1 | 10/2001 | Smith et al. | 435/297.5 |
| 6,323,022 B1 | 11/2001 | Chang et al. | 435/286.5 |
| 6,410,309 B1 | 6/2002 | Barbera-Guillem et al. | 435/297.5 |
| 6,455,310 B1 | 9/2002 | Barbera-Guillem | 435/383 |
| 6,465,243 B2 | 10/2002 | Okada et al. | 435/301.1 |
| 6,468,792 B1 | 10/2002 | Bader | 435/325 |
| 6,518,035 B1 | 2/2003 | Ashby et al. | 435/18 |
| 6,548,263 B1 | 4/2003 | Kapur et al. | 435/7.2 |
| 6,555,365 B2 | 4/2003 | Barbera-Guillem et al. | 435/303.1 |
| 6,569,675 B2 | 5/2003 | Wall et al. | 435/304.2 |
| 6,576,458 B1 | 6/2003 | Sarem et al. | 435/286.5 |
| 6,588,586 B2 | 7/2003 | Abasolo et al. | 206/204 |
| 6,593,136 B1 | 7/2003 | Geiss | 435/325 |
| 6,653,124 B1 | 11/2003 | Freeman | 435/297.1 |
| 6,673,595 B2 | 1/2004 | Barbera-Guillem | 435/286.2 |
| 6,759,245 B1 | 7/2004 | Toner et al. | 435/401 |
| 6,794,184 B1 | 9/2004 | Mohr et al. | 435/294.1 |
| 6,811,752 B2 | 11/2004 | Barbera-Guillem | 422/100 |
| 6,818,438 B2 | 11/2004 | Muser | 435/304.3 |
| 6,821,772 B2 | 11/2004 | Barbera-Guillem et al. | 435/297.5 |
| 6,841,384 B2 | 1/2005 | Robbins, Jr. | 435/325 |
| 6,855,542 B2 | 2/2005 | DiMilla et al. | 435/289.1 |
| 6,908,767 B2 | 6/2005 | Bader | 435/395 |
| 7,022,518 B1 | 4/2006 | Feye | 435/297.1 |
| 7,078,228 B2 | 7/2006 | Lacey et al. | 435/288.1 |
| 7,160,687 B1 | 1/2007 | Kapur et al. | 435/7.2 |
| 7,192,769 B2 | 3/2007 | Pykett et al. | 435/373 |
| 7,195,758 B2 | 3/2007 | Schultze et al. | 424/93.71 |
| 2002/0039785 A1 | 4/2002 | Schroeder et al. | 435/304.3 |
| 2002/0110905 A1 | 8/2002 | Barbera-Guillem et al. | 435/294.1 |
| 2003/0008388 A1 | 1/2003 | Barbera-Guillem et al. | 435/297.5 |
| 2003/0008389 A1 | 1/2003 | Carll | 435/302.1 |
| 2003/0040104 A1 | 2/2003 | Barbera-Guillem | 435/286.2 |
| 2003/0143727 A1 | 7/2003 | Chang | 435/289.1 |
| 2004/0029266 A1 | 2/2004 | Barbera-Guillem | 435/297.5 |
| 2004/0043481 A1 | 3/2004 | Wilson | 435/297.1 |
| 2004/0072347 A1 * | 4/2004 | Schuler et al. | 435/372 |
| 2004/0132175 A1 | 7/2004 | Vetillard et al. | 435/297.1 |
| 2005/0009179 A1 | 1/2005 | Gemmiti et al. | 435/420 |
| 2005/0032208 A1 | 2/2005 | Oh et al. | 435/366 |
| 2005/0077225 A1 | 4/2005 | Usher et al. | 210/321.6 |
| 2005/0101009 A1 | 5/2005 | Wilson et al. | 435/295.3 |
| 2005/0106717 A1 | 5/2005 | Wilson et al. | 435/297.5 |
| 2005/0169962 A1 | 8/2005 | Bhatia et al. | 424/423 |
| 2005/0260745 A1 | 11/2005 | Domansky et al. | 435/294.1 |
| 2006/0003436 A1 | 1/2006 | DiMilla et al. | 435/284.1 |
| 2006/0019361 A1 | 1/2006 | Ng et al. | 435/177 |
| 2006/0031955 A1 | 2/2006 | West et al. | 800/24 |
| 2006/0112438 A1 | 5/2006 | West et al. | 800/17 |
| 2006/0121606 A1 | 6/2006 | Ito et al. | 435/325 |
| 2006/0136182 A1 | 6/2006 | Vacanti et al. | 703/11 |
| 2006/0141617 A1 | 6/2006 | Desai et al. | 435/325 |
| 2006/0252150 A1 | 11/2006 | Cheng | 435/372 |
| 2007/0026516 A1 * | 2/2007 | Martin et al. | 435/297.5 |
| 2007/0166822 A1 * | 7/2007 | Kenney et al. | 435/325 |

FOREIGN PATENT DOCUMENTS

| | | |
|---|---|---|
| EP | 0 725 134 | 8/1996 |
| EP | 0 890 636 | 10/2001 |
| GB | 1 539 263 | 1/1979 |
| WO | WO 90/05179 | 5/1990 |
| WO | WO 91/15570 | 10/1991 |
| WO | WO 00/56870 | 9/2000 |
| WO | WO 00/78932 | 12/2000 |
| WO | WO 01/92462 | 12/2001 |
| WO | WO/02/066595 | 8/2002 |
| WO | WO 03/085080 | 10/2003 |
| WO | WO 2004/106484 | 12/2004 |
| WO | WO 2005/035728 | 4/2005 |

OTHER PUBLICATIONS

Kamel Mamchaoui and Georges Saumon, A method for measuring the oxygen consumption of intact cell monolayers, American Journal of Physiology Lung Cellular and Molecular Physiology (2000) 278: L858-L863.

Derwent Abstract for EP155236.

E. Barbera-Guillem, "Overcoming cell culture barriers to meet the demands of cell biology and biotechnology", Reprinted from American Biotechnology Laboratory, May 2001.

"Cell Culture Equipment (Hardware & Devices)", Lab Times, Products, Jan. 2006, pp. 52-58.

* cited by examiner

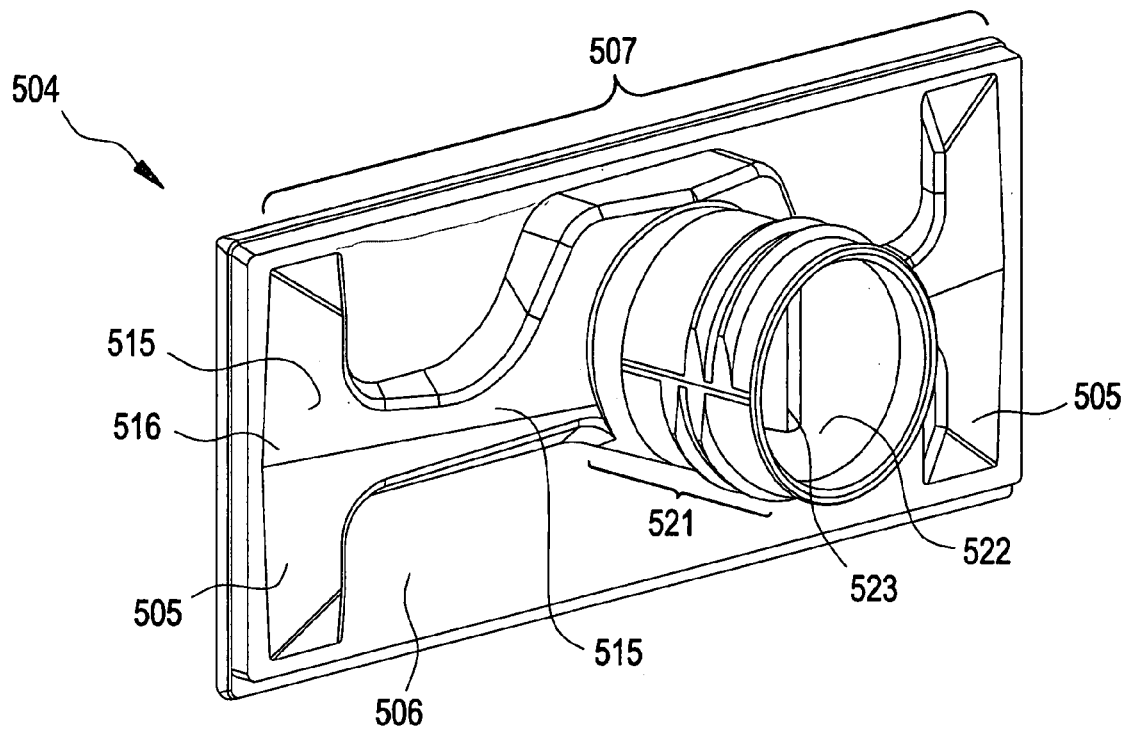
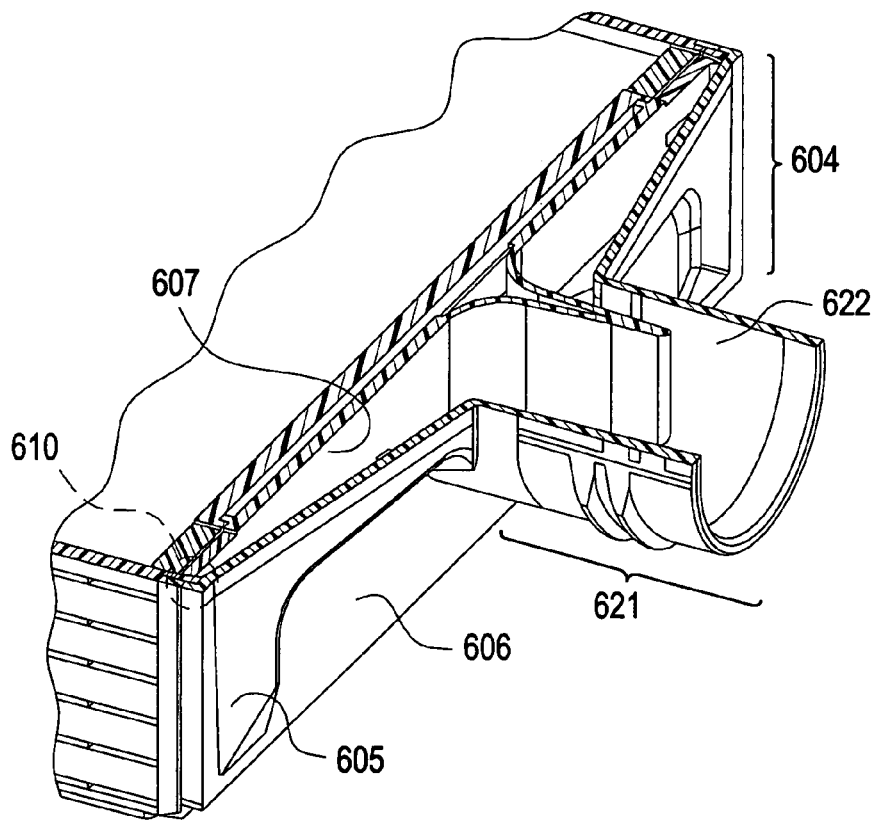

DEVICE AND METHOD FOR REDUCING BUBBLE FORMATION IN CELL CULTURE

FIELD OF THE INVENTION

The present invention relates generally to a device for reducing the formation of bubbles or foam in cell culture, and, in particular, to a device for directing cell culture media into a cell culture vessel to minimize the mixing of the media with air, and thereby minimizing the formation of bubbles or foam inside the cell culture vessel.

BACKGROUND OF THE INVENTION

In vitro culturing of cells provides material necessary for research in pharmacology, physiology, and toxicology. Recent advances in pharmaceutical screening techniques allow pharmaceutical companies to rapidly screen vast libraries of compounds against therapeutic targets. These large-scale screening techniques require large numbers of cells grown and maintained in vitro. Maintaining these large numbers of cells requires large volumes of cell growth media and reagents and large numbers and types of laboratory cell culture containers and laboratory equipment. This activity is also labor intensive.

Cells are grown in specialized cell culture containers including roller bottles, cell culture dishes and plates, multi-well plates, microtiter plates, common flasks and multi-layered cell growth flasks and vessels. An exemplary flask for creating a suitable environment for culturing cells is a common laboratory flask. Cells in culture attach to and grow on the bottom surface(s) of the flask, immersed in a suitable sustaining media.

With the advent of cell-based high throughput applications, cell culture vessels have been developed to provide an increased surface area for cell growth while also providing necessary gas exchange. These systems also employ traditional cell culture vessels including common flasks, roller bottles, cell culture dishes, as well as multi-layered cell growth vessels including multi-layer flasks, multi-layer cell culture dishes, bioreactors, and the like, which may include specialized surfaces designed to enhance the cell culture parameters including growth density and differentiation factors.

In addition, cell-based high throughput applications have become automated. Automation permits manipulation of the cell culture vessel much like that performed by the manual operator. Further, flask vessels having multiple layers of cell growth are capable of producing a greater cell yield than commonly known flasks that permit growth of cells on a single bottom wall. While these multiple layer vessels allow for the growth of large numbers of cells, they present special challenges in day to day use.

In some high density cell culture vessels, each cell culture layer inside the flask or vessel has multiple ports to direct the flow of cells and cell culture media into the vessel. These systems for directing the flow of cells and cell culture media into and out of these high density vessels provide locations for cell culture media and air to mix, creating bubbles or foam.

Introducing cell culture media into these vessels in excess of that necessary for cell growth has been one way to reduce the formation of foam inside these vessels. However, cell growth media can be quite expensive, and the use of excess cell growth media is not desirable.

There is a need for a cell culture vessel that can provide a device to direct media into a cell culture vessel in a way that reduces the formation of bubbles or foam inside the container. There is also a need for a high density cell culture vessel that may incorporate such a device. There is a need for high density cell culture vessels that reduce the formation of bubbles and reduce the amount of cell culture media needed for the cell culture vessel to operate properly. In addition, there is a need for such a device that may be suitable for use in the performance of high throughput assay applications that commonly employ robotic manipulation.

SUMMARY OF THE INVENTION

According to embodiments of the present invention, a device and method for reducing bubbles and foam in cell culture is disclosed. In particular, a device which has a manifold for directing cell culture media into a multi-layer cell culture vessel to minimize the mixing of the media with air, and thereby to minimize the formation of bubbles or foam inside the multi-layer cell culture vessel is disclosed. A method of using the device is also disclosed.

According to an embodiment of the invention, a manifold is disclosed. The manifold directs and separates the in-flow of liquid and out-flow of gas through a cell culture vessel. In an embodiment, the manifold has a necked opening which is attached to a shoulder structure to form a neck/shoulder structure, where the neck/shoulder structure is attached to a barrier plate and where the neck/shoulder structure encompasses apertures which are holes through the barrier plate which allow liquid introduced into the neck of the manifold to flow through one side of the neck/shoulder structure and through the apertures into a cell culture vessel while allowing air displaced by the inflow of liquid to escape the cell culture vessel by passing through apertures through the barrier plate on the other side of the neck/shoulder structure, through the neck/shoulder structure and out through the necked opening.

In addition, a method of culturing cells using the cell growth apparatus of the present invention comprises steps of: providing a cell growth apparatus of the present invention, introducing cells and/or media into said cell growth apparatus in a tilted filling position, filling the internal volume, closing the opening, positioning or tilting the apparatus to a horizontal cell growth position, and then incubating the apparatus.

In another embodiment, a manifold for directing in-flow of liquid and outflow of gas through a cell culture vessel is disclosed. The manifold has a necked opening with an opening and an interior surface, an inflow shoulder and an outflow shoulder, and a barrier plate structured and arranged to attach to a cell culture vessel. The inflow shoulder and outflow shoulder are attached to the barrier plate and to the neck, and the inflow shoulder and outflow shoulder each have interior surfaces. The interior surface of the neck is adjacent to and continuous with the interior surfaces of the inflow shoulder and the outflow shoulder. The inflow shoulder and the outflow shoulder each have at least one aperture through the barrier plate so that liquid introduced into the necked opening flows through the necked opening into the inflow shoulder, through the inflow aperture into the cell culture vessel, and gas displaced by the liquid entering the cell culture vessel is vented out of the cell culture vessel through the aperture of the outflow shoulder, into the outflow shoulder, and out through the necked opening.

In an embodiment the manifold is integral with the cell culture vessel or, in another embodiment, the manifold is releasably attached to the cell culture vessel. Or, in another embodiment that is attached to the cell culture vessel by ultrasonic welding, laser welding, solvent bonding or the application of an adhesive. In another embodiment, the inflow shoulder and the outflow shoulder are attached to the barrier plate by an ultrasonic welding, laser welding, solvent bonding or the application of an adhesive. In an embodiment the cell culture vessel is a flask or a multi-layer flask. In another embodiment the shoulder openings are structured and arranged to align with cell culture media spaces in the multi layer flask.

In yet another embodiment, the present invention is a device for reducing the formation of bubbles inside a cell culture vessel which has a manifold structured and arranged to attach to a cell culture vessel. The cell culture vessel has an interior space structured and arranged to contain cells in culture. The manifold has a barrier plate, a neck, a first shoulder and a second shoulder. The first shoulder and second shoulder have interior surfaces. The neck has a top opening, an interior surface and a septum. The septum is continuous with the interior surface of the neck and divides the neck into two liquid impermeable neck sections, each having an interior surface. The interior surface of each neck section is continuous with the interior surface of an adjacent shoulder. Both shoulders are connected to the barrier plate each shoulder has at least one aperture through the barrier plate into the interior space of the cell culture vessel. When liquid is introduced into the neck through the top opening, liquid flows through one neck section into the adjacent shoulder and through at least one aperture into the interior space of the cell culture vessel.

In a further embodiment, the multi-layer cell culture vessel has a manifold for directing the in-flow of liquid and the out-flow of gas through the cell culture vessel where the manifold has a barrier plate, an inflow shoulder, an outflow shoulder and a neck, and the inflow shoulder and outflow shoulder have interior surfaces. The neck has a top opening an interior surface and a septum which is continuous with the interior surface of the neck, and the septum divides the neck into two liquid impermeable neck sections, a liquid inflow neck section and a gas outflow neck section, each neck section having an interior surface. The interior surface of the liquid inflow neck section is adjacent to and continuous with the interior surface of the inflow shoulder and the interior surface of the gas outflow neck section is adjacent to and continuous with the interior surface of the outflow shoulder. The inflow and outflow shoulders are connected to the barrier plate. Each shoulder has at least one shoulder opening through the barrier plate into the interior space of the multi-layer cell culture vessel and at least one shoulder opening is aligned with at least one cell culture media containing space in the multi-layer cell culture vessel.

In an embodiment, when liquid is introduced into the liquid inflow neck section through the top opening, the liquid flows through the liquid inflow neck section, into the adjacent inflow shoulder, through at least one shoulder opening into the cell culture media containing space of the multi-layer cell culture vessel, and gas displaced by the liquid entering cell culture media containing space of the multi-layer cell culture vessel flows out of the multi-layer cell culture vessel, through at least one shoulder opening, into the outflow shoulder and through the gas outflow neck section.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

FIG. 5 is a perspective view of a manifold of the present invention.

FIG. 6 is a cross-sectional perspective view of an embodiment of the present invention.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Increasingly, cell cultures are grown in stacked, space saving high density containers which minimize incubator space and maximize cell culture growth surface. As cell culture containers become more and more efficient, and the spaces within them become more and more restricted, the practical use of these containers becomes complicated by the need to move small quantities of liquids into and out of these containers. One problem associated with the movement of liquid into and out of cell culture containers is the production of bubbles and foam inside cell culture containers. If protein-rich cell culture media is mixed with air or gas, bubbles or foam tend to form. These bubbles can be quite difficult to remove, especially from the small confines of high-density cell culture containers. Bubbles can interfere with cell growth, cause inconsistent cell growth, and introduce operator error into a controlled laboratory environment. Once bubbles or foam exist inside the small spaces of cell culture containers, it can be extremely difficult to remove them. It might be necessary to discard an expensive high density cell culture container rather than attempt to remove a persistent bubble.

In some multi-level cell culture containers, multiple ports exist on each cell culture layer to allow for the flow of cells and cell culture media into and out of the cell culture environment. As these small spaces are filled with cells and liquid media, air that is displaced from this environment must leave the cell culture environment. If displaced air leaves the enclosed cell culture environment through the path of the inflowing media, the incoming liquid media mixes with the outgoing air and bubbles and foam form.

Figure 1:
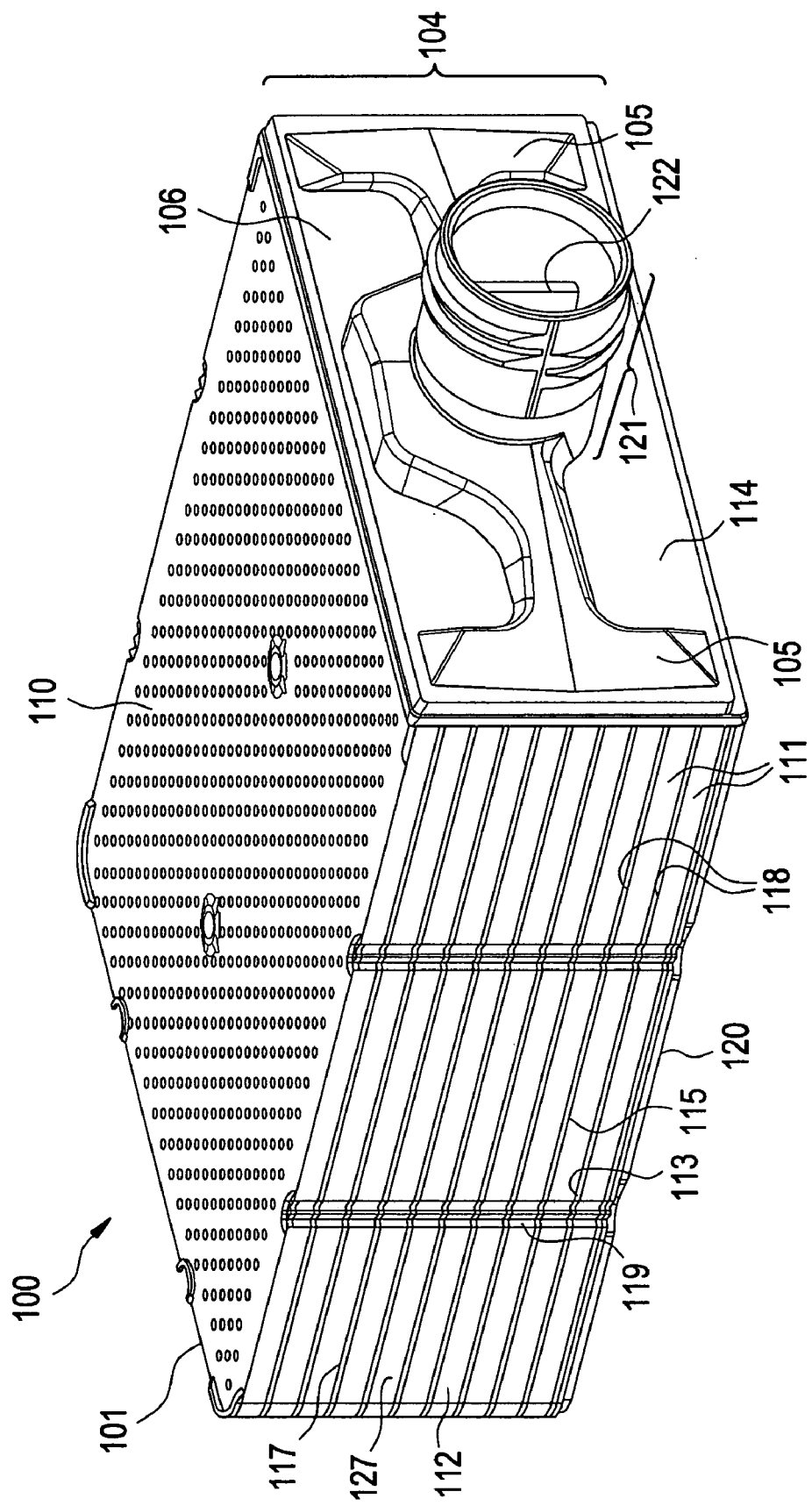
FIG. 1 is an external view of an embodiment of the multi-layer flask and manifold of the present invention.

An external view of a flask apparatus that can be used in accordance with one embodiment of the manifold of the present invention is shown in FIG. 1. The flask 100 comprises an outer vessel body 101 defined by a top plate 110, a bottom tray 120, sidewalls 112, and end walls 114. Disposed within the flask 100 are individual cell growth chambers 111 as can be seen more clearly in the cut-away illustration in FIG. 2.

The individual cell growth chambers 111 are each defined by a generally transparent bottom surface 113 and a generally transparent top surface 115. The surfaces 113 and 115 are attached to the flask body 101 along the sidewalls 112 and end walls 114. Preferably, at least one bottom surface 113 within each chamber 111 is a gas permeable, liquid impermeable material and capable of providing a surface for the growth of cells 117. Each top surface 115 is preferably a rigid, generally gas impermeable material (preferably transparent) that will provide support to the cell growth chamber 111. In this embodiment, supports 119 allow a gas permeable membrane 113 to be securely adhered thereto in a leak-proof sealing to the flask body 101. Tracheal spaces 118 are created between each cell growth chamber 111. The opposing top surface 115 of the chamber 111 defines an upper wall to the cell growth chamber 111 as well as a bottom portion of a tracheal chamber 118. The tracheal chamber 118 is therefore inclusive of a gas permeable, liquid impermeable surface 113 of a first cell growth chamber and an opposing surface 115 to a second growth chamber 111. Supports 119 further provide structural arrangements to integrally incorporate the surfaces 113 and 115 in forming growth chambers 111 in alternation with tracheal air spaces 118 within the unitary flask 101. Each cell growth chamber 111 therefore alternates with a tracheal chamber 118 in vertical successive orientation. Accessibility to the cellular growth chambers 111 is achieved via a necked opening 121 within the flask body 101.

FIG. 1 illustrates an embodiment of the present invention having a necked opening 121 connected to the cell growth chambers 111 via a manifold 104. The manifold 104 is a portal for manipulation of flask contents. The manifold 104 has a necked opening 121 which is continuous with shoulder sections 105. The neck section and the shoulder sections are the neck/shoulder section. The neck/shoulder section is attached to a barrier plate 106 which is attached to the cell culture vessel and forms an end wall 114 of the cell culture vessel. In this embodiment, the necked opening 121 has a septum 122. The necked opening can be covered by a cap (not shown) allowing the flask to be completely filled with media 127 without leakage. The cap may be present or absent. If present, the cap may incorporate filters to allow for the exchange of gas between the internal and external spaces of the cell culture system.

In one embodiment of the present invention, the individual cell growth chambers 111 permit cellular growth on gas permeable membranes 113 such that multiple cell growth chambers 111 are integral with the body 101 of the apparatus 100 and are capable of being completely filled with nutrient media for the growth of cells. The series of tracheal air spaces 118 through the apparatus 100 provide gaseous communication between the cells 117 growing on gas permeable surfaces 113, in media 127 in the individual cell growth chambers 111 inside the apparatus, and the external environment. The tracheal spaces 118 allow oxygenation of media located within cell growth chambers 111 through the gas permeable surfaces 113. Further, the tracheal chambers 118 may take the form of any air gap or space, and do not allow entrance of liquid. As a result, a rigid cell culture apparatus 100 having multiple growth chambers 111, alternating with tracheal spaces 118, is cooperatively constructed to afford the benefit of equivalent gaseous distribution to a large volume of cells 117.

Figure 2:
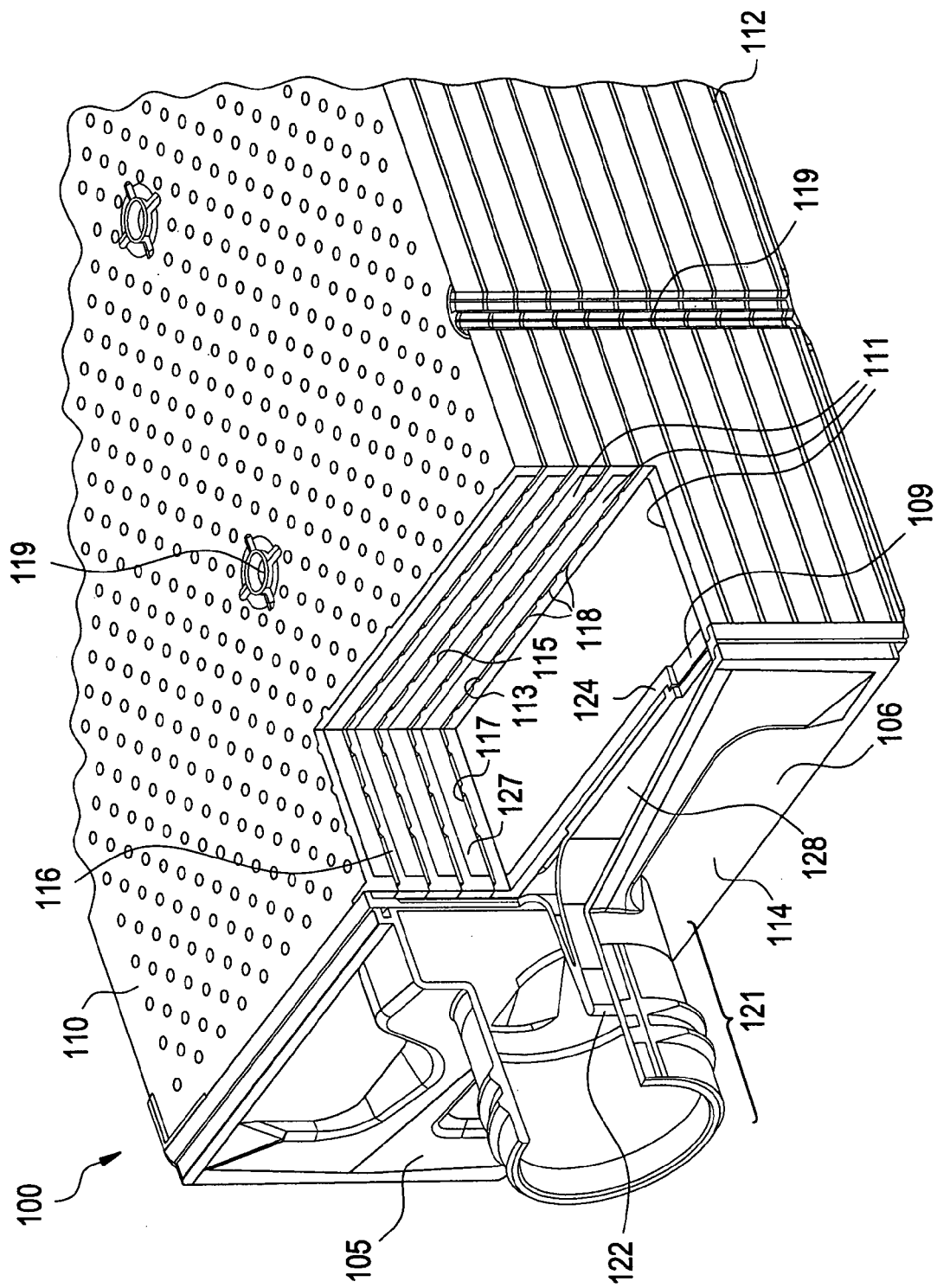
FIG. 2 is a partial cut-away view of an embodiment of the multi-layer flask and manifold of the present invention.

FIG. 2 is a partial cut-away view of an embodiment of the present invention FIG. 2 illustrates alternating layers of tracheal air spaces 118 and individual cell growth chambers 111 which form the interior of flask 100. The individual cell growth chambers 111 are defined by liquid impermeable, gas permeable membranes 113 attached in a liquid-impermeable manner to the sidewalls and endwalls of the cell culture vessel. Cell growth media 127 is contained between the membranes 113 and cells grow on the liquid-surface of these membranes 113. In this embodiment, the cell growth chamber 111 may be formed by two layers of gas permeable membrane attached in a liquid impermeable manner to sidewalls 112 to form an individual cell growth chamber 111. Tracheal air spaces 118 form layers between the gas permeable membranes, forming air pockets to allow the gas permeable membranes 113 to exchange air into the cell growth media 127. In this embodiment, tracheal air spaces are supported by supports 119 which separate and support the layers of gas permeable membrane 113 which form individual cell growth chambers 111. An advantage of this embodiment of the multi-layered flask that is compatible with an embodiment of the manifold of the present invention is its enhanced capacity to grow cells on an opposing surface when the apparatus is rotated 180°. Thus, when the apparatus is rotated, cells can be cultured on an alternate gas permeable membrane surface 113. Where only gas permeable membranes are layered intermediary to the apparatus, cell growth is therefore enabled on both of its gas permeable surfaces 113.

Gas permeable, liquid impermeable membranes 113 may be made of one or more membranes known in the art. Membranes typically are made of suitable materials that may include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. As manufacturing and compatibility for the growth of cells permits, various polymeric materials may be utilized. For its known competency, then, polystyrene may be a preferred material for the membrane (of about 0.003 inches in thickness, though various thicknesses are also permissive of cell growth). As such, the membrane may be of any thickness, preferably between about 25 and 250 microns, but ideally between approximately 25 and 125 microns.

The membrane 113 allows for the free exchange of gases between the individual cell culture growth chamber 111 and tracheal spaces 118. A preferred embodiment would include a membrane 113 that is additionally durable for manufacture, handling, and manipulation of the apparatus.

FIG. 2 illustrates, in an embodiment, an individual cell growth chamber 111. The interior of the individual cell growth chamber 111 of the embodiment shown in FIG. 2 does not freely communicate with the necked opening 121 of the multi-layer cell culture vessel. The barrier plate 106 separates the neck-end 124 of the individual cell growth chambers 111 from the necked opening 121 of the multi-layer flask. Communication between the necked opening 121 of the multi layer flask of an embodiment of the present invention and the individual cell growth chambers 111 of an embodiment of the present invention is through the aperture 109 at each end of the individual cell growth chambers 111.

The gas permeable membrane 113 can be affixed to supports 119 and side walls 112 by any number of methods including but not limited to adhesive or solvent bonding, heat sealing or welding, compression, ultrasonic welding, laser welding and/or any other method commonly used for generating seals between parts. Laser welding around the circumference of the membrane 113 is preferred to establish a hermetic seal around the membrane region such that the membrane is flush with and fused to the face of the supports 119 such it becomes an integral portion of the interior surface of the apparatus. Once the gas permeable membrane 113 is adhered to the sidewalls and endwalls, the top plate 110 and bottom tray 120 may be joined. The bottom tray 120 and top plate 110 may be injection molded. Various sizes and shapes of the supports 119 may be incorporated to facilitate positioning of the membranous layers 113 for cell culture 117 within the cell culture vessel 100.

The apparatus 100 of the present invention may be made by any number of acceptable manufacturing methods well known to those of skill in the art. In an embodiment of a method, the apparatus 100 is assembled from a collection of separately injection molded parts. Although any polymer (such as polystyrene, polycarbonate, acrylic, polystyrene, or polyester) suitable for molding and commonly utilized in the manufacture of laboratory ware may be used, polystyrene is preferred. Although not required, for optical clarity, it is advantageous to maintain a thickness of no greater than 2 mm. The separate parts may be assembled by any number of methods including but not limited to: adhesive or solvent bonding, heat sealing or welding, compression, ultrasonic welding, laser welding and/or any other method commonly used for generating seals between parts such that it becomes an integral portion of the interior surface 128 of the apparatus. The top plate 110 and bottom tray 120 may be aligned and joined, such as by laser welding. When a cap is provided, it may be a screw cap, snap-fit cap, cap with septum, cap with air holes, cap with integral filter or other device for gas exchange or any cap known in the art. In one embodiment, the cap can be removably positioned on a necked opening to prevent access to the contents of the apparatus 100 via the manifold 104 on an end wall 114.

In an embodiment, the parts are held together and are adhesive bonded along the seam, ultrasonically welded, or laser welded. Preferably, laser welding equipment is utilized in a partially or fully automated assembly system. The top plate and tray are properly aligned while a laser weld is made along the outer periphery of the joint.

Advantageously and in order to enhance cell attachment and growth, the surfaces internal to the apparatus 100, including the membrane layer, may be treated to enable cell growth. Treatment may be accomplished by any number of methods known in the art which include plasma discharge, corona discharge, gas plasma discharge, ion bombardment, ionizing radiation, and high intensity UV light.

In an alternative embodiment, an individual cell growth chamber may be bounded on one side by a layer of gas permeable membrane 110, attached in a liquid impermeable manner to sidewalls 112 and on another side by a top surface that is a rigid layer, to provide a more rigid element to the individual cell culture growth chamber 111 and the multi-layered flask as a whole. For example, an individual cell growth chamber 111, bounded on a top side by a rigid layer 115, on its edges by sides, and on a bottom side by a gas permeable membrane. This individual cell growth chamber 111 can be stacked on top of another such individual cell growth chamber 111, where the top portion of a rigid layer 115 of one individual cell growth chamber 111 forms a support structure that defines tracheal spaces underneath a gas permeable membrane 113 of the adjacent individual cell growth chamber. In this embodiment, individual cell culture chambers can be assembled into a larger multi-layer cell culture vessel. These individual layers can be snapped together, or otherwise attached to each other using any attachment method known in the art.

In another embodiment of the flask of the present invention, cell growth media in individual cell growth chambers 111 do not mix, as the individual cell growth chambers 111 are separate from each other, and can be modular units for easy assembly and disassembly of the flask unit.

Figure 3:
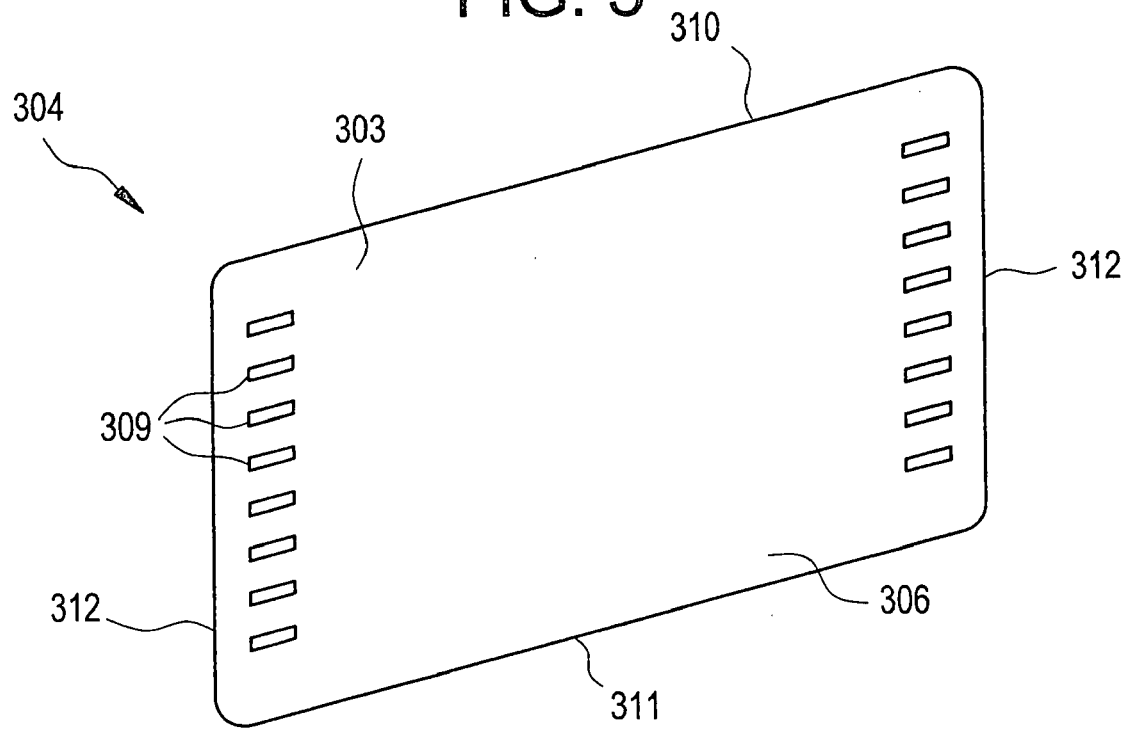
FIG. 3 is a perspective view of an embodiment of the flask-surface of a manifold of the present invention.

FIG. 3 is a perspective view of an embodiment of the flask-surface 303 of a manifold 304 of the present invention. The manifold 304 is illustrated in FIG. 5. When completely assembled, the layers of the multiple layered cell culture vessel are attached in a liquid impermeable manner to the flask-surface 303 of the barrier plate 306 of the manifold 304, and the top plate 110, bottom tray 120 and side walls 112 of the cell culture vessel 100 (see FIG. 1.) are attached in a liquid impermeable manner to the top end 310, bottom end 311 and sides 312 of the manifold 304.

Figure 4:
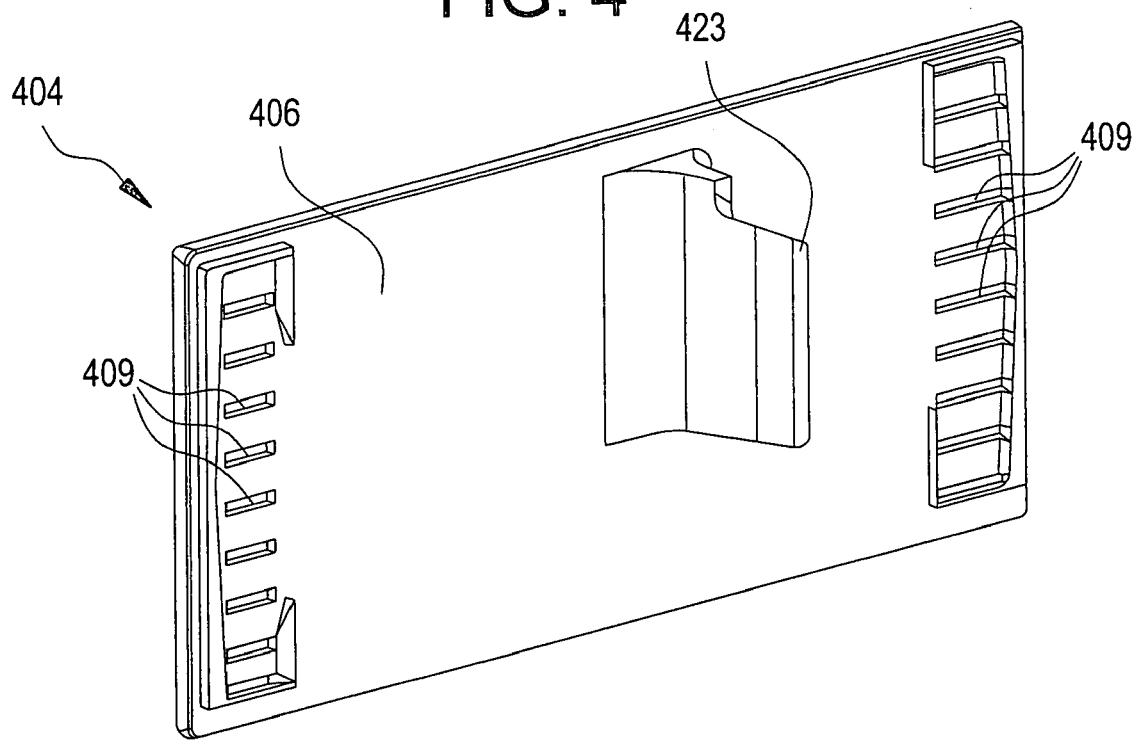
FIG. 4 is a perspective view of the interior surface of an embodiment of the manifold of the present invention with the shoulder and neck structures removed.

FIG. 3 illustrates the flask-surface 303 of the manifold, which forms an end wall of the multi-layered cell culture vessel and has apertures 309. Apertures 309 are holes through the barrier plate 306 which forms the neck-end or end wall (114, see FIG. 1) of the cell culture vessel, and also forms the bottom layer of the manifold 304 of the present invention (see FIG. 5). In an embodiment of the present invention, media and cells can flow into each layered cell growth chamber 111 (see FIG. 2) only through apertures 309 through the barrier plate 306. The flask-surface of the manifold 304 is illustrated in FIG. 3, the top surface of the barrier plate (with the neck and shoulder structure removed) is illustrated in FIG. 4, and the manifold with the neck and shoulder structure is illustrated in FIG. 5. When the barrier plate 306, as illustrated in FIG. 3, is attached to or forms an end wall of a cell culture vessel, the apertures 309 are aligned with the layered cell growth chambers so that the interior space of the manifold (see FIG. 5) is in communication with the individual cell growth chambers through the apertures 309. Because the barrier plate forms an end wall, when the cell culture vessel is assembled, the barrier plate prevents the contents of each layered cell growth chamber from flowing into and out of the layered cell growth chambers and into a necked opening at an end of a cell culture vessel, except through the apertures 309. Liquid cell culture media can only flow into and out of a cell culture vessel through these apertures 309. The barrier plate, which is the bottom layer of the manifold 304, and also forms an end wall of the cell culture vessel, creates a pathway for the flow of liquid into a cell culture vessel and the flow of displaced air out of a cell culture vessel.

The barrier plate 306 may be an end wall of a flask with an inflow aperture and an outflow aperture through the end wall, aligned with each layer of the cell growth chamber. Or, in an alternative embodiment, the barrier plate 306 may be attached to an open-ended multi-layer cell culture vessel where the barrier plate fits or snaps into the open-ended multi-layer cell culture vessel to create an inflow aperture and an outflow aperture at the end of the cell culture vessel and functions to restrict the inflow and outflow of liquid and gas to a defined flow circuit. In an embodiment, the open-ended multi-layer cell culture vessel may be assembled by stacking individual cell culture units together, and then attaching a manifold as shown in FIG. 5, to the stack of individual open-ended cell culture layers. Or, in an alternative embodiment, the barrier plate may not be a separate piece, but may be formed when multiple separate cell growth chambers, each having an inflow aperture and an outflow aperture, are stacked one on top of another to form an assembled cell culture vessel made up of multiple layers, where liquid access to the individual cell growth chambers via a necked opening is restricted to a defined flow circuit. In yet another alternative embodiment, the manifold may be releasably attached to a cell culture vessel in a gasket or compressive fit (like Tupperware®).

FIG. 3 illustrates that the flask-surface 303 of the barrier plate 306 of a manifold 304 of the present invention has apertures 309. The group of apertures on one side or the other side of the barrier plate 306 is a set of apertures. These apertures 309 align with the individual cell growth chambers of the cell culture vessel, creating the only access into and out of the individual cell growth chambers (111, see FIG. 2) of an embodiment of the present invention. Cells and cell culture media can be delivered to and extracted from the multi-layer cell culture vessel through these apertures. Although in operation, one set of apertures will function as the inflow apertures and the other set of apertures will function as the outflow apertures, these sets of apertures may be identical, and the difference between the inflow and the outflow apertures may be simply the orientation of the cell culture vessel at the time of the introduction of liquid into the vessel.

An embodiment of the manifold 504 of the present invention is shown in FIG. 5. The manifold 504 functions to direct and separate the in-flow of liquid and outflow of gas through a cell culture vessel. The manifold 504 has a barrier plate 506 attached to an inflow shoulder 505, and an outflow shoulder 505. These shoulders 505 are continuous with a necked opening 521. Together, the shoulders and the necked opening create a shoulder/neck section 507.

FIG. 6 is a cross-sectional perspective view of an embodiment of the present invention. FIG. 6. illustrates that interior surface 622 of the necked opening 621 of the embodiment of the manifold 604 of the present invention is continuous with the interior surface 607 of the shoulders 605. In an embodiment, the manifold of the present invention may be attached to the multi-layer cell culture vessel by means of an attachment 610. This may be a releasable pressure-attachment like a snapping hook, or a permanent attachment such as a welded seam. The shoulder/neck section (see 507, FIG. 5) may be formed as a separate molded part and attached to the barrier plate 606 by any means, including adhesive bonding along the seam, ultrasonic welding, or laser welding. Preferably, laser welding equipment is utilized in a partially or fully automated assembly system and the shoulder/neck structure 507 and the barrier plate 606 are properly aligned while a laser weld is made along the outer periphery of the joint.

FIG. 4 is a perspective view of the interior surface of an embodiment of the manifold of the present invention with the shoulder/neck structure (see FIG. 5) removed. FIG. 4 shows the barrier plate 406, which contains the apertures 409 through the barrier plate 406 and creates access into the individual cell growth chambers (see 111 in FIGS. 1 and 2) of the multi-layer cell growth container of an embodiment of the present invention. As illustrated in FIG. 4, an embodiment of a manifold of the present invention places the barrier plate between the necked opening (see FIG. 5) and access to the individual cell growth chambers (see FIGS. 1 and 2) of the cell culture vessel. The necked opening (See FIG. 1 121, FIG. 5 521 and FIG. 6 621) forms the opening for the flask 100 (see FIGS. 1 and 5). Cell culture media and cells may be introduced into the flask, and removed from the flask through the necked opening 121. The necked opening 121 of the flask 100 may be resealable by way of a cap (not shown) that can be removably attached to the necked opening 121 to prevent contents of the flask from spilling.

FIG. 4 also illustrates that an embodiment of the present invention may have a septum 423. As illustrated in FIG. 5, in this embodiment, the septum 523 is a liquid impermeable barrier which separates one side of the necked opening from the other side of the necked opening, and also separates the interior space inside the manifold that is bounded by the barrier plate 506 below, the septum 523 on the medial side and the shoulder 505 on the top side 515 and outside edge 516 of the manifold 504. FIG. 4 illustrates an embodiment of the septum. The septum may be manufactured as an integral part of the barrier plate of the manifold, or it may be manufactured as a separate piece which is attached to the necked opening and the barrier plate by any means including adhesive bonding along the seam, ultrasonic welding, or laser welding.

Figure 7:
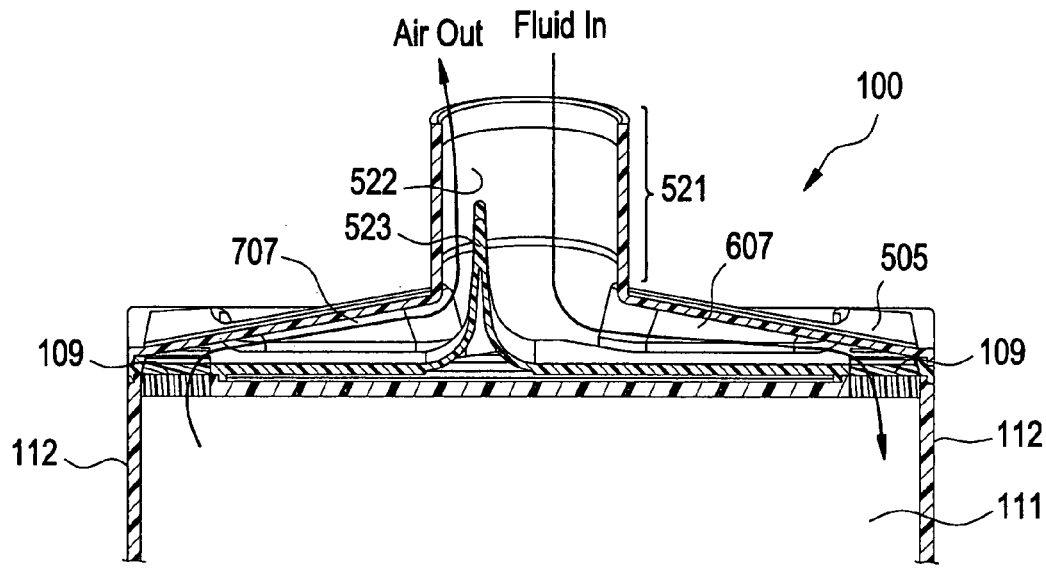
FIG. 7 is a cross-sectional view of an embodiment of the present invention illustrating the flow of liquid into and air out of the embodiment.
Figure 8:
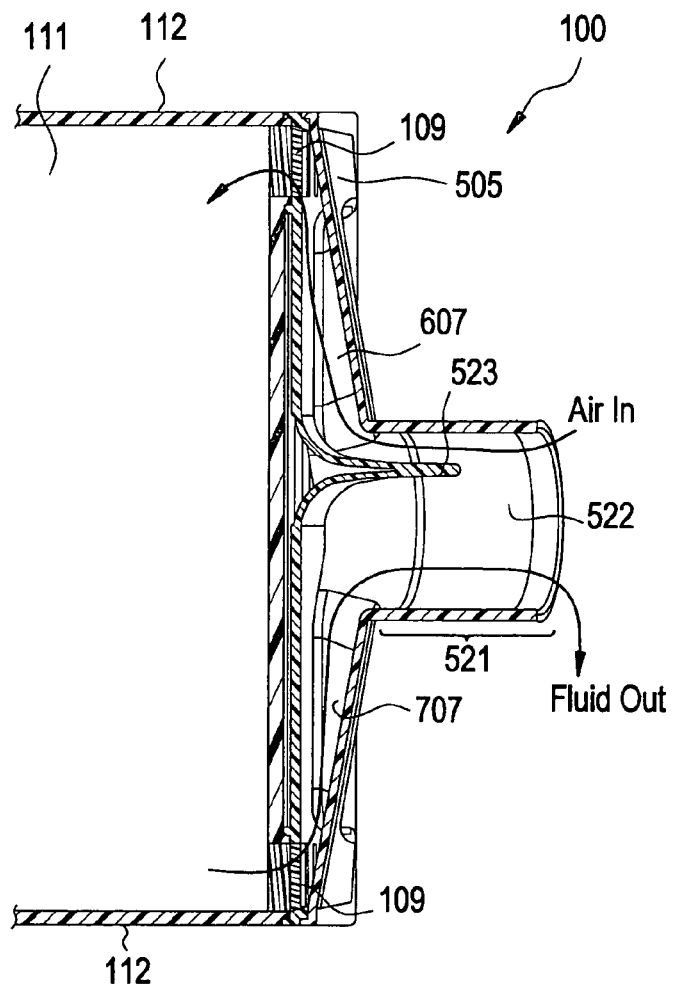
FIG. 8 is a cross-sectional view of an embodiment of the present invention illustrating the flow of liquid out of and air into the embodiment.

In an embodiment of the present invention, when the septum 523 is present, the interior surface of the necked opening is separated into two interior spaces. FIGS. 7 and 8 illustrate the position of the septum 523. The interior surfaces 522 of the necked opening 521 are adjacent to and continuous with the interior surfaces 607 of shoulder, which interior surfaces define shoulder interior spaces 707. Shoulder interior spaces 707 contain apertures 109 leading from the shoulder interior spaces 707 to the individual cell growth chambers 111. FIG. 7 illustrates a method of filling an embodiment of the apparatus of the present invention, FIG. 7 illustrates the flow of cells and cell media into an embodiment of the present invention. Liquid media and cells flow into the embodiment of the invention in the "fluid in" side of the necked opening 521. Liquid media and cells are directed to one side of the flask of the present invention by the septum 523. Thus directed, liquid media and cells flow through the interior shoulder space 707, through the apertures 109, and into individual cell growth chambers 111. Depending upon the orientation of the cell culture vessel when liquid is introduced into the flask, the neck interior space and the shoulder interior space on one side of the flask of an embodiment of the present invention may provide a course for either fluid in or air out. That is, in an embodiment of the present invention, either shoulder of the manifold can be an "inflow shoulder" or an "outflow shoulder" depending upon the direction of flow of liquid media into or out of the apparatus of the present invention.

By introducing cell culture media into the cell culture vessel in this way, air or gas that is displaced from the individual cell growth layers upon the introduction of liquid media can escape through the apertures located on the other side of an embodiment of the flask of the present invention and exit the cell culture vessel through the "air out" side of the necked opening 521 of the apparatus. By directing cell culture media through the cell culture system in this way, cell culture media enters the cell culture vessel through a defined inflow route and displaced air or gas exits the cell culture system through a defined outflow route so that the entering cell culture media and the exiting air or gas do not flow through the same stream, and the opportunity for cell culture media to mix with air is limited, limiting the formation of bubbles or foam inside the cell culture vessel.

FIG. 8 is a cross-sectional view of an embodiment of the present invention illustrating a method of using an embodiment of the present invention. In some embodiments, the apparatus of the present invention will be used to remove liquid media from the flask of the present invention. Liquid media and cells flow can flow out of the individual cell growth chambers through the "fluid out" side of the necked opening 521. Air can flow into the embodiment of the apparatus of the present invention through the "air in" side of the apparatus. Liquid media and cells are separated from the incoming air by the septum 523. Thus directed, liquid media and cells flow from the individual cell growth chambers, through aperture 109, through the interior shoulder space 707 and out via the necked opening 521. By directing cell culture media out of the cell culture system in this way, cell culture media and air do not mix and the formation of bubbles or foam inside the cell culture vessel is reduced.

In addition, in an embodiment of the present invention, because the barrier plate forms an end wall for each layer of cell culture inside a multi-well plate, it may not be necessary to completely fill areas, such as neck areas, which contain cell culture media that is shared among all the layers of cell culture. Therefore, use of an embodiment of the manifold of the present invention in association with multi-layer cell culture vessels may result in the utilization of less cell culture media.

In an embodiment of the present invention, the shoulder/neck section may be shaped to control the flow of liquid inside the shoulder/neck section. For example the shoulder area may be shaped in a roughly tubular shape, before flaring out to encompass the apertures that remain open to the individual cell culture layers at each end of the manifold.

It will be understood by a skilled artisan that the inflow side of the necked opening, the inflow shoulder and the inflow apertures, and the outflow side of the necked opening, the outflow shoulder and the second set of apertures are interchangeable. That is, either shoulder and either set of apertures can be the first shoulder and the first set of apertures and either shoulder and either set of apertures can be the second shoulder and the second set of apertures, depending upon the orientation of the cell culture vessel at the time of the introduction of liquid into the cell culture system. In an alternative embodiment, certain features may create a more favorable pathway for the introduction of liquid or for the exhaust of air or gas in the system. For example, in one embodiment, the septum may be shaped or oriented inside the necked opening to allow for easier introduction of liquid into one side or the other of the cell culture system. In alternative embodiments, the septum may be curved or better accommodate the tip of a pipette or other instrument used to contain cell culture media to introduce into the cell culture vessel. Or, the septum may, in one embodiment of the present invention, be placed off-center inside the necked opening so that the inflow side of the necked opening constitutes approximately four-fifths of the interior volume of the necked opening, while the remaining one-fifth of the volume of the necked opening serves as the outflow side, to allow the passage of air out of the cell culture vessel.

The introduction of cell culture media into the cell culture system may be accomplished by tipping the cell culture flask so that one shoulder is up and the other shoulder is down, thereby using gravity to introduce cell culture media into the first shoulder, through the first set of apertures, and assisting with the controlled flow of cells and cell culture media into the cell culture vessel and the controlled escape of gas or air from the individual cell growth chambers through the second set of apertures, through the second shoulder and out through the necked opening.

In an alternative embodiment, the septum may or may not be present inside the necked opening of the manifold of the present invention. If the septum is not present, the introduction of cell culture media into one side of the cell culture system may be accomplished solely by tipping the apparatus and using gravity to direct cell culture media into the individual cell growth chambers through the lower shoulder. It will be apparent to one having ordinary skill in the art that the shape and orientation of the septum within the necked opening can be varied to optimize the utility of the cell culture system of the present invention and that these variations are within the scope of the disclosed invention.

The flask and manifold apparatus 100 in accordance with an embodiment of the present invention is employed according to accepted cell growth methods. Cells are introduced to the apparatus 100 though the apertures 109 via the necked opening 121. Along with the cells 117, media 127 is introduced such that the cells are immersed in the media. It will be understood by an ordinarily skilled artisan that any discussions herein describing cell culture media also include cell culture media which contains cells. The apparatus is arranged such that the cell containing media covers the cell growth surfaces 113. Advantageously, the apparatus 100 is capable of being completely filled with media since the gas permeable membranes 113 in combination with the tracheal spaces 118 provide uniform gas distribution to the cell growth surfaces 113. This will further ensure the flow and exchange of gases between the flask interior and the external environment. The apparatus is then placed within an incubator and may be stacked together with similar vessels such that a number of cell cultures are simultaneously grown. The apparatus is situated such that the bottom tray 120 assumes a horizontal position (or vertical position depending on the cell culture application).

Cell growth may be monitored from time to time by microscopic or visual inspection through the generally transparent interior and exterior surfaces of the apparatus 100. Easier accessibility and greater visibility of cellular growth can be visualized when optical lenses having varying magnifications are employed in the external body 101. Optical lenses provide confirmation that no extraneous gas or bubbles exist within the individual cell growth chambers.

Additionally, during the cell growth process, it may become necessary to extract the exhausted media and insert fresh media. This can be accomplished by tipping the flask and allowing the exhausted media to pour out of the flask via the necked opening. New media can be introduced into the same flask by the same process as described above. Once cells are ready for harvesting, a chemical additive such as trypsin is added to the apparatus through the necked opening. The trypsin has the effect of releasing cells from the surfaces of the apparatus. The cells can then be removed from the flask by pouring the cell containing cell culture medium out of the flask.

Although a flask embodiment is illustrated in the figures, the directional-flow manifold of the present invention can be incorporated into any type of cell culture vessel known to those of ordinary skill in the art. These well-known alternative cell culture vessels include bioreactors, roller bottles and stackable devices.

Other embodiments of an apparatus/vessel of the present invention may incorporate raised corners, posts, ledges, stand-offs or any other feature that will allow spacing between successively stacked flasks. The standoffs may be molded onto an exterior surface of the apparatus and may be cast at any angle, having any size or dimension to facilitate growth of cells away from extraneous gases/bubbles. The stand-offs further ensure lateral stability of the stacked vessels. The manifold is further capable of including a diversified arrangement of projections to trap extraneous gas or bubbles in multiple gas collection areas.

In addition, a method of culturing cells using the cell growth apparatus of the present invention comprises steps of: providing a cell growth apparatus of the present invention, introducing cells and/or media into said cell growth apparatus in a tilted filling position, filling the internal volume, closing the opening, positioning or tilting the apparatus to a horizontal cell growth position, and incubating the apparatus.

The apparatus may include any unitary structure, vessel, device or flask that would benefit from a directional inflow and outflow of liquid and air into and from an internal volume. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A manifold for directing in-flow of liquid and out-flow of gas through a cell culture vessel comprising:
   a necked opening comprising an opening and an interior surface;
   an inflow shoulder and an outflow shoulder;
   a barrier plate structured and arranged to attach to a cell culture vessel;
   wherein the inflow shoulder and outflow shoulder are attached to the barrier plate and to the neck;
   wherein the inflow shoulder and outflow shoulder each have interior surfaces;
   wherein the interior surface of the neck is adjacent to and continuous with the interior surfaces of the inflow shoulder and the outflow shoulder;
   wherein the inflow shoulder and the outflow shoulder comprise at least one aperture through the barrier plate;
   whereby liquid introduced into the necked opening flows through the necked opening into the inflow shoulder, through the inflow aperture into the cell culture vessel, and gas displaced by the liquid entering the cell culture vessel is vented out of the cell culture vessel through the aperture of the outflow shoulder, into the outflow shoulder, and out through the necked opening.

2. The manifold of claim 1 wherein the manifold is integral with the cell culture vessel.

3. The manifold of claim 1 wherein the manifold is releasably attached to the cell culture vessel.

4. The manifold of claim 1 wherein the manifold is attached to the cell culture vessel by a method comprising: ultrasonic welding, laser welding, solvent bonding or the application of an adhesive.

5. The manifold of claim 1 wherein the inflow shoulder and the outflow shoulder are attached to the barrier plate by a method comprising: ultrasonic welding, laser welding, solvent bonding or the application of an adhesive.

6. The manifold of claim 1 wherein the cell culture vessel is a flask.

7. The culture vessel of claim 6 wherein the culture vessel is a multi-layer flask.

8. The culture vessel of claim 7 wherein the shoulder openings are structured and arranged to align with cell culture media spaces in the multi layer flask.

9. A device for reducing the formation of bubbles inside a cell culture vessel comprising:
   a manifold structured and arranged to attach to a cell culture vessel;
   wherein the cell culture vessel has an interior space structured and arranged to contain cells in culture;
   wherein the manifold comprises a barrier plate, a neck, a first shoulder and a second shoulder, said first shoulder and second shoulder having interior surfaces;
   wherein the neck comprises a top opening and an interior surface;
   wherein the neck further comprises a septum;
   wherein the septum is continuous with the interior surface of the neck and
   wherein the septum divides the neck into two liquid impermeable neck sections, each having an interior surface;
   wherein said interior surface of each neck section is continuous with the interior surface of an adjacent shoulder;
   wherein said first and second shoulders are connected to the barrier plate;
   wherein each shoulder comprises at least one aperture through the barrier plate into the interior space of the cell culture vessel;
   whereby when liquid is introduced into the neck through the top opening, said liquid flows through one neck section into the adjacent shoulder and through said at least one aperture into the interior space of the cell culture vessel.

10. The manifold of claim 9 wherein the manifold is integral with the cell culture vessel.

11. The manifold of claim 9 wherein the manifold is releasably attached to the cell culture vessel.

12. The manifold of claim 9 wherein the manifold is attached to the cell culture vessel by a method comprising: ultrasonic welding, laser welding, solvent bonding or the application of an adhesive.

13. The manifold of claim 9 wherein the inflow shoulder and the outflow shoulder are attached to the barrier plate by a method comprising: ultrasonic welding, laser welding, solvent bonding or the application of an adhesive.

14. The manifold of claim 9 wherein the cell culture vessel is a flask.

15. The culture vessel of claim 14 wherein the culture vessel is a multi-layer flask.

16. The culture vessel of claim 15 wherein the shoulder openings are structured and arranged to align with cell culture media spaces in the multi layer flask.

17. A multi-layer cell culture vessel comprising:
   a manifold for directing the in-flow of liquid and the outflow of gas through the cell culture vessel wherein the manifold comprises a barrier plate, an inflow shoulder, an outflow shoulder and a neck, said inflow shoulder and outflow shoulder having interior surfaces;
   wherein the neck comprises a top opening and an interior surface;
   wherein the neck further comprises a septum;
   wherein the septum is continuous with the interior surface of the neck and
   wherein the septum divides the neck into two liquid impermeable neck sections, a liquid inflow neck section and a gas outflow neck section, each neck section having an interior surface;
   wherein the interior surface of the liquid inflow neck section is adjacent to and continuous with the interior surface of the inflow shoulder and the interior surface of the gas outflow neck section is adjacent to and continuous with the interior surface of the outflow shoulder;
   wherein said inflow and outflow shoulders are connected to the barrier plate;
   wherein each shoulder comprises at least one shoulder opening through the barrier plate into the interior space of the multi-layer cell culture vessel;
   wherein the at least one shoulder opening is aligned with at least one cell culture media containing space in the multi-layer cell culture vessel;
   whereby when liquid is introduced into the liquid inflow neck section through the top opening, said liquid flows through the liquid inflow neck section, into the adjacent inflow shoulder, through said at least one shoulder opening into the cell culture media containing space of the multi-layer cell culture vessel, and gas displaced by the liquid entering cell culture media containing space of the multi-layer cell culture vessel flows out of the multi-layer cell culture vessel, through said at least one shoulder opening, into the outflow shoulder and through the gas outflow neck section.

18. The manifold of claim 17 wherein the manifold is integral with the cell culture vessel.

19. The manifold of claim 17 wherein the manifold is releasably attached to the cell culture vessel.

20. The manifold of claim 17 wherein the manifold is attached to the cell culture vessel by a method comprising: ultrasonic welding, laser welding, solvent bonding or the application of an adhesive.

21. The manifold of claim 17 wherein the inflow shoulder and the outflow shoulder are attached to the barrier plate by a method comprising: ultrasonic welding, laser welding, solvent bonding or the application of an adhesive.

* * * * *